United States Patent [19]

Gorvel

[11] Patent Number: Plant 6,134

[45] Date of Patent: Mar. 22, 1988

[54] DWARF SCHEFFLERA NAMED COVETTE

[76] Inventor: Ernest A. Gorvel, 800 St. Lucie Cresent, Stuart, Fla. 33495

[21] Appl. No.: 820,809

[22] Filed: Jan. 22, 1986

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Schwartz, Jeffery, Schwaab, Mack, Blumenthal & Evans

[57] ABSTRACT

A new cultivar of *Schefflera arboricola*, named Covette, combines the characteristics of leaf glossiness, dwarf habit, vigor and good propagation by stem cuttings, among others.

2 Drawing Figures

BACKGROUND OF THE INVENTION

The present invention relates to a new and distinctive cultivar of schefflera plant named Covette. Covette is a sport of an unnamed cultivar of *Schefflera arboricola*. The parent cultivar is unpatented but available commercially.

The genus Schefflera includes over 150 widely-distributed species of shrubs and trees of the family Araliaceae. These species typically have compound leaves (racks), the leaflets of which are arranged finger-fashion, and are generally long-stalked. One species from Australia, *S. actinophylla*, is thought by some to comprise a separate genus (Brassaia). In any event, *S. actinophylla* is popular as a house plant, having glossy-green, lanceolate leaflets, usually 5 to 7 per cluster, that have some serration.

Another Schefflera species of Taiwanese origin, *S. arboricola* (also known as "Hawaiian Elf"), is a freely branching plant of dwarf habit, resembling when young a miniature Brassaia (*S. actinophylla*). The obovate-shaped leaflets of *S. arboricola* are arranged in racks of up to 15 cm across, comprising 7 to 8 leaflets. While the combination in *S. arboricola* of hardy dwarf habit and tree-like appearance is desirable, a dull (non-glossy) leaf has contributed to making *S. arboricola* less popular as a decorative plant than *S. actinophylla*.

The new cultivar of the present invention was discovered by me in Stuart, Fla., as a mutation of an unnamed plant of *S. arboricola*. More specifically, the mutation was observed initially as a single branch growing from one plant of the parent cultivar, in a cultivated area. By asexual reproduction, via soil-rooted stem cuttings, of the new cultivar in Stuart, Fla., I have reproduced the unique features of the new cultivar through successive propagations. The cultivar, as asexually reproduced, is characterized by a compact form (approximately 30 inches wide and 38 inches high) and, like the parent cultivar, by vigorous growth, but additionally possesses foliage that differs substantially from the parent cultivar, for example, in leaf size, shape and texture.

DESCRIPTION OF THE DRAWING

The first sheet depicts a typical specimen of 'Covette'; and,

The second sheet depicts the large leaved parent; *S. arboricola* held by hand (with watch), and 'Covette' (hand held).

DETAILED BOTANICAL DESCRIPTION

The accompanying colored photographs illustrate the new cultivar and show, as clearly as it is reasonably possible, the differences in plant form and foliage that distinguish the new cultivar from the parent and from other cultivars of this species with which I am familiar. The photograph comprising sheet 1 is a perspective view of a schefflera plant, approximately six months in age, of my new cultivar Covette.

The photograph comprising sheet 2 is a close-up, comparative view of foliage racks of the parent cultivar, Covette, and a typical commercial cultivar of the species *S. actinophylla*, respectively. More specifically, an *S. actinophylla* rack appears in the foreground of the photograph; some three to four racks of *S. arboricola*, the parent, appear in the upper left; and a rack of my new cultivar is seen just right of center. (Above the aforesaid Covette rack, in the upper right corner of the photograph, is another immature rack of the new cultivar, comprising leaflets approximately six weeks in age.) Because the photograph was taken in direct sunlight, the leaf colors do not correspond precisely to those reported in the following table. However, the leaflet glossiness of my new cultivar, comparing favorable with the relative dullness of the parent, is readily apparent.

The following table provides a detailed description of my new Schefflera cultivar based on plants produced under commercial practices in the test fields of Florida Cuttings, Inc. (Stuart, Fla.). Color references are made to The Royal Horticultural Society Colour Chart (R.H.S.) except where general color terms of ordinary dictionary significance have been used. The table compares the noted characteristics of Covette with the same characteristics of its parent cultivar, with a further comparison being made to a typical commercial cultivar of the species *S. actinophylla*.

The leaves of the new cultivar, like those of the parent, are generally smooth-edged and lacking in serrations. But the leaves of the parent cultivar are thicker and less pliable (are "harder") than the leaves of the new cultivar, which also has a glossy leaf texture that is quite unlike the dull leaf texture of the parent *S. arboricola*. Thus, the new cultivar possesses the much desired leaf glossiness which is characteristic of *S. actinophylla*. In other aspects, such as leaf length and internodal distance, the new cultivar is situated in appearance somewhere between *S. actinophylla* and the parent cultivar, *S. arboricola.* The stem color of *S. actinophylla,* for example, has a decidedly purple tinge, while *S. arboricola* stem color is a solid, medium green. The stem color of my new cultivar, on the other hand, is dark green with purple discontinuities.

My new cultivar is also unusually disease- and pest-resistant. For example, the new cultivar will flourish without treatment with pesticides over an extended period which would leave the parent, if similarly untreated, severely damaged by aphids and other insects. Unlike *S. actinophylla,* Covette is resistant to a wide variety of diseases, including scale, and is generally resistant to infestation, e.g., by spider mites which typically infest *S. actinophylla* plants.

As mentioned previously, the new cultivar is readily propagated asexually by stem cuttings. Indeed, Covette plants grown for seven years have yet to produce seed, while *S. arboricola* plants generally bear seed after three to four years of growth. (By contrast, *S. actinophylla* plants usually must be grown ten years or longer before producing seed.) In addition, a stem cutting of my new cultivar can be rooted in soil and grown to commercial size (approximately 36 inches tall) in only some four months, or about twice as fast as required to carry out the same procedure for a *S. arboricola* stem cutting.

The following chart summarizes the outstanding characteristics of 'Covette' compared with *S. actinophylla* and *S. arboricola:*

| Foliage Description | New Cultivar | *S. arboricola* (parent cultivar) | *S. actinophylla* |
|---|---|---|---|
| Leaf Shape: | oblanceolate | obovate, with acuminate tip | lanceolate, with acuminate tip |
| Average Leaf Length: (approx.) | 13.3 cm | 7.4 cm | 19.3 cm |
| Leaf Thickness/ Pliability: | medium | hard | soft |
| Leaf Texture: | glossy | nonglossy | glossy |
| Color of Foliage (mature): | dark green, approximating RHS 147A | dark green, approximating RHS 147A | medium green approximating RHS 146A |
| Average Stem Length (approx.): | 18.3 cm | 9.7 cm | 24.1 cm |
| Internodal Distance | 5.0–7.6 cm | 2.5–4.4 cm | 1.9–6.3 cm (significant variation) |
| Ribs & Veins | larger and fewer than parent; about 1.9 cm apart | many tiny veins; about 0.6 cm apart | many small veins; about 0.6 cm apart |
| Leaflets (and coverage) per rack: | 7–8 (up to 25 cm) | 7–8 (up to 15 cm) | 5–7 (up to 30 cm) |
| Disease & Pest Resistance: | generally resistant to disease and infestation | susceptible to aphids disease and | susceptible to a wide variety of pests |

*Measurements conducted together, in normal sunlight at about 2:11 p.m. (EST), on December 27, 1985, in Stuart, Florida, using plants of about the same age (6 months) which were raised under substantially the same growing conditions (approximate average temperature: 75° F.)

I claim:

1. A new and distinct cultivar of *Schefflera arboricola* named Covette as herein shown and described, characterized particularly as to uniqueness by the combined characteristics of dark green foliage; oblanceolate-shaped leaves of approximately 13 centimeters in length; glossy leaf texture; good propagation by stem cuttings; and disease and pest resistance.

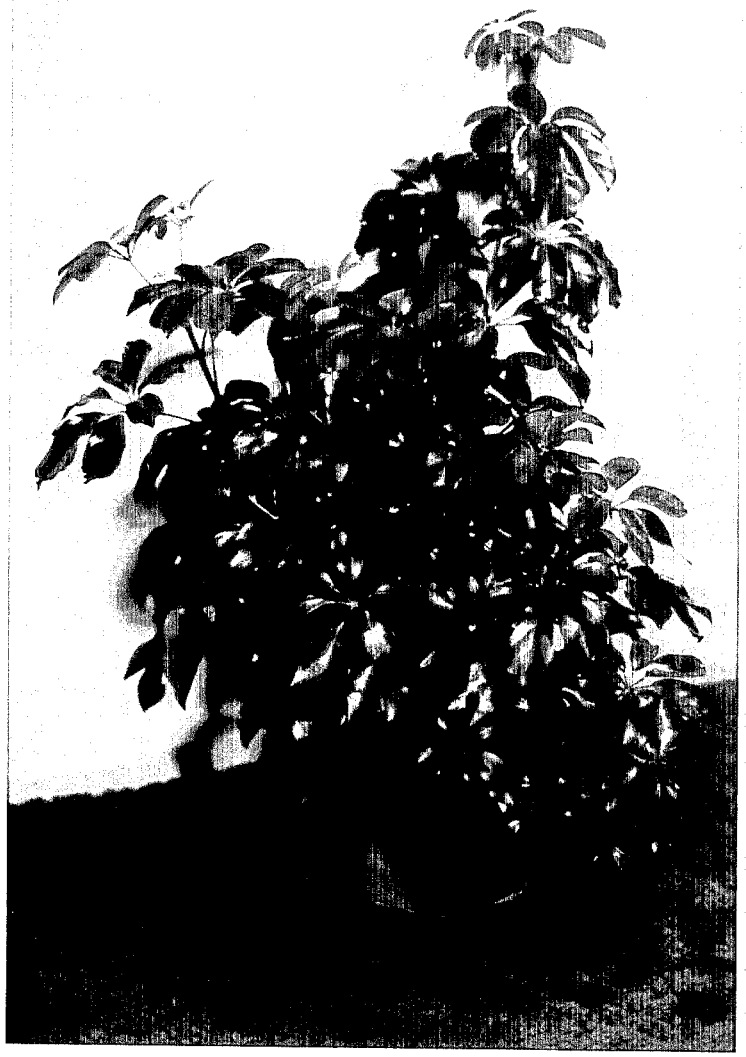

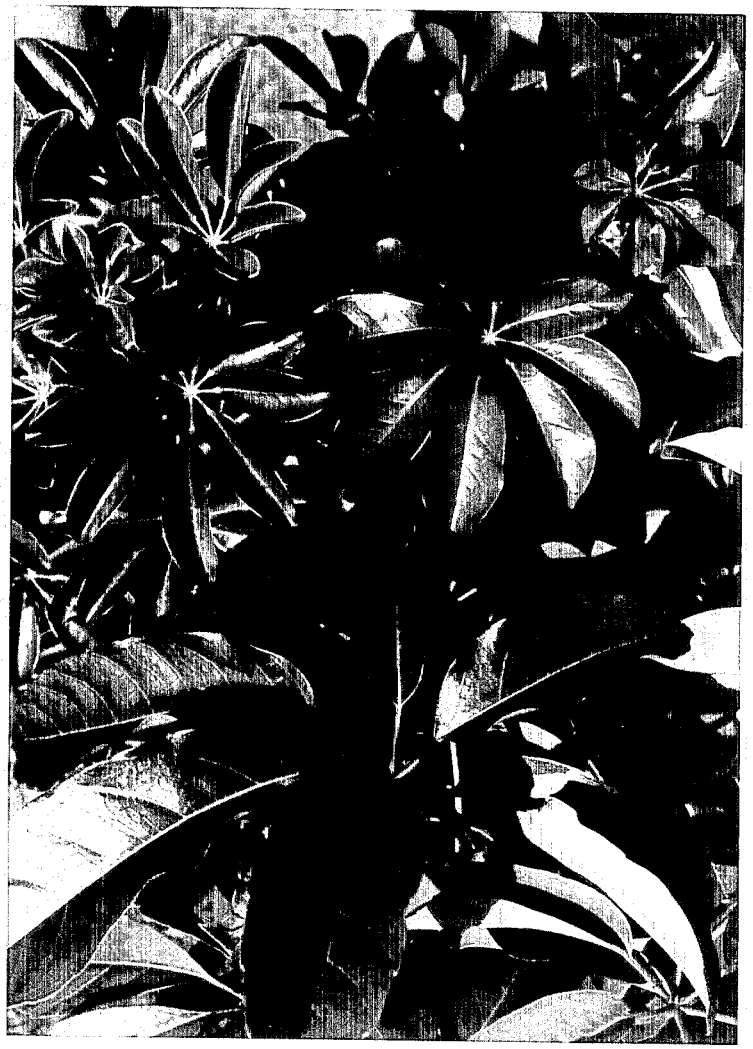

* * * * *